United States Patent [19]

Soldati

[11] Patent Number: 4,976,849
[45] Date of Patent: Dec. 11, 1990

[54] FRACTIONATION PROCESS FOR GASEOUS HYDROCARBON MIXTURES WITH A HIGH ACID GAS CONTENT

[75] Inventor: Gian F. Soldati, Milan, Italy
[73] Assignee: Snamprogetti S.p.A., Milan, Italy
[21] Appl. No.: 246,744
[22] Filed: Sep. 20, 1988
[30] Foreign Application Priority Data
  Sep. 25, 1987 [IT] Italy .................. 22030 A/87
[51] Int. Cl.⁵ ............................... F25J 3/02
[52] U.S. Cl. ............................. 208/351; 62/17; 62/23; 62/24
[58] Field of Search ............... 208/351, 354, 355; 62/11, 17, 23, 24, 44

[56] References Cited

U.S. PATENT DOCUMENTS

| | | | |
|---|---|---|---|
| 2,880,592 | 4/1959 | Davidson et al. | 62/23 |
| 3,150,199 | 9/1954 | Greco et al. | 62/24 X |
| 4,150,962 | 4/1979 | Colton | 208/351 X |
| 4,351,655 | 9/1982 | Styring, Jr. | 62/24 X |
| 4,459,142 | 7/1984 | Goddin, Jr. | 62/17 |
| 4,563,202 | 1/1986 | Yao et al. | 62/17 |
| 4,753,666 | 6/1988 | Pastor et al. | 62/24 |
| 4,761,167 | 8/1988 | Nicholas et al. | 62/17 |

Primary Examiner—Glenn Caldarola
Attorney, Agent, or Firm—Oblon, Spivak, McClelland, Maier & Neustadt

[57] ABSTRACT

A fractionation process for gaseous hydrocarbon mixtures of high acid gas content is described, for separating at least a fraction containing ethane, propane and heavier hydrocarbons, a fraction containing essentially acid gases and a fraction containing essentially methane and possible inert gases, characterized by comprising the following stages:

(a) feeding the gaseous hydrocarbon mixture after dehydration to a first distillation column to which a liquid hydrocarbon stream is fed, to obtain a gaseous overhead product stream containing methane, ethane, acid gases and possibly light inert gases, and a bottom product stream containing ethane and higher hydrocarbons;

(b) feeding the overhead product of the first distillation column to a second distillation column to obtain a gaseous overhead product stream containing methane, the ethane-carbon dioxide azeotrope and possibly light inert gases, and a bottom product stream consisting essentially of acid gases;

(c) feeding the overhead product of the second distillation column to a third distillation column the condenser of which is injected with a liquid hydrocarbon stream, to obtain a gaseous overhead product stream consisting essentially of methane and possibly inert gases, and a bottom product stream which is recycled to the first column and contains the ethane-carbon dioxide azeotrope and the liquid hydrocarbon stream injected into the condenser;

(d) feeding the bottom product of the first distillation column to a fourth distillation column to obtain a gaseous overhead product stream containing ethane and a bottom product stream containing higher hydrocarbons than butane.

34 Claims, 4 Drawing Sheets

FRACTIONATION PROCESS FOR GASEOUS HYDROCARBON MIXTURES WITH A HIGH ACID GAS CONTENT

This invention relates to a fractionation process for gaseous hydrocarbon mixtures with a high acid gas content. More particularly, the invention relates to a process for recovering ethane and heavy hydrocarbons and for removing acid gases such as carbon dioxide and hydrogen sulphide by distillation from gaseous hydrocarbon mixtures which contain them, such as natural gas, synthesis gas or associated gases.

The purpose of the process according to the present invention is to separate a fraction formed of ethane, propane and heavier hydrocarbons, a fraction formed essentially of acid gases, and a fraction formed essentially of methane and possible insert gases (such as nitrogen) and having an acid gas content such as to satisfy the specific requirements for pipeline feed and for gas liquefaction. A fractionation process of the known art is described hereinafter from the teachings of A. S. Holmes and J. M. Ryan given in U.S. Pat. No. 4,350,511 and in "Hydrocarbon Processing" (April 1984 page 71) "Ryan-Holmes Technologies". Said process comprises essentially the following stages:

feeding the gaseous mixture to a first distillation column also fed with a liquid hydrocarbon stream, in which the carbon dioxide/ethane split is made to obtain an overhead stream containing methane and carbon dioxide and a bottom stream containing ethane and higher hydrocarbons;

feeding the overhead stream from the first column, after compression and cooling, to a second distillation column in which the methane/carbon dioxide split is made to obtain an overhead methane and acid gas stream and a bottom acid gas stream;

feeding the overhead stream of the second distillation column to a third distillation column also fed with a liquid hydrocarbon stream to obtain an overhead methane stream and a bottom carbon dioxide stream;

feeding the bottom product of the first distillation column to a fourth distillation column in which the propane/butane split is made to obtain an overhead stream containing ethane and propane and a bottom stream containing butane and higher hydrocarbons which is partly recycled to the first and third distillation columns.

The major drawback of this process is its high absorbed power and the considerable heat energy required, due mainly to the large throughputs of the recycled liquid hydrocarbon streams.

A new process has been found which results in a considerable reduction in energy consumption mainly by recycling smaller liquid hydrocarbon stream throughputs while at the same time increasing the percentage of ethane recovery.

According to the present invention, the fractionation process for gaseous hydrocarbon mixtures of high acid gas content, such as natural gas, synthesis gas or associated gases, for separating at least a fraction containing ethane, propane and heavier hydrocarbons, a fraction containing essentially acid gases and a fraction containing essentially methane and possibly inert gases, is characterised by comprising the following stages:

(a) feeding the gaseous hydrocarbon mixture after dehydration to a first distillation column (decarbonater column) to which a liquid hydrocarbon stream is fed, to obtain a gaseous overhead product stream containing methane, ethane, acid gases and possibly light inert gases, and a bottom product stream containing ethane and higher hydrocarbons;

(b) feeding the overhead product of the first distillation column to a second distillation column (deazeotroper column) to obtain a gaseous overhead product stream containing methane, the ethane-carbon dioxide azeotrope and possibly light inert gases, and a bottom product stream consisting essentially of acid gases;

(c) feeding the overhead product of the second distillation column to a third distillation column (demethanizer column) the condenser of which is injected with a liquid hydrocarbon stream, to obtain a gaseous overhead product stream consisting essentially of methane and possibly inert gases, and a bottom product stream which is recycled to the first column and contains the ethane-carbon dioxide azeotrope and the liquid hydrocarbon stream injected into the condenser;

(d) feeding the bottom product of the first distillation column to a fourth distillation column to obtain a gaseous overhead product stream containing ethane and a bottom product stream containing higher hydrocarbons than butane.

The overhead product of the fourth distillation column can contain essentially only ethane (in which case the bottom product also contains propane and butane), or can also contain propane (in which case the bottom product also contains butane), or can also contain propane and butane (in which case the bottom product contains only hydrocarbons higher than butane).

The gaseous hydrocarbon mixture to be fractionated can be cooled and partially condensed before feeding to the first distillation column.

The first distillation column operates at a pressure preferably of between 10 and 40 ata and at an overhead temperature preferably of between −45° and +10° C.

Before being fed to the second distillation column, the overhead product of the first distillation column can be partially condensed and the liquid obtained be separated from the gas, which can then be further partially condensed, and the separated liquid and the partially condensed gas can finally be fed to the second distillation column.

The second distillation column operates at a pressure preferably of between 10 and 50 ata and an overhead temperature preferably of between −50° and −10° C.

Before being fed to the third distillation column, the overhead product of the second distillation column can be compressed and possibly cooled.

With this possible cooling, said product may be partially condensed, in which case the liquid obtained is separated from the gas which is again condensed, the separated liquid and the partially condensed gas finally being fed to the third distillation column.

The third distillation column operates at a pressure preferably of between 15 and 50 ata and a temperature preferably exceeding carbon dioxide solidification temperature, and more preferably of between −57° and 0° C.

The liquid hydrocarbon stream injected into the condenser of the third distillation column can consist essentially of only propane or only butane or only pentane, or butane and higher hydrocarbons, or pentane and higher hydrocarbons. The two liquid hydrocarbon streams can be of identical or different composition.

The two liquid hydrocarbon streams can also originate directly from a part of the bottom product of the fourth distillation column or can originate from a fractionation run effected on the bottom product of the fourth distillation column.

The liquid hydrocarbon stream to the first distillation column is preferably fed into the column rectification section, i.e., between the feed of the gaseous hydrocarbon mixture to be fractionated and the column condenser.

The bottom product of the third distillation column fed to the first distillation column is preferably fed into the stripping section of the first column, i.e., between the feed of the gaseous hydrocarbon mixture to be fractionated and the column reboiler. The molar ratio of the liquid hydrocarbon stream fed to the first distillation column, to the ethane in this first column is preferably between 3 and 20.

In addition, the hydrocarbon stream must be fed to the first distillation column at several points on the column.

The bottom product of the second distillation column can be expanded and the produced cold used for cooling other process streams.

The reboiler of the second distillation column can also be used to recover cold.

Cold make-up can be obtained by a refrigeration cycle with mechanical compression using either pure refrigerant fluids or mixed refrigerant fluids.

For example, a mechanical compression refrigeration cycle employing mixed propane/carbon dioxide fluid can be preferably used in which the required minimum temperature is obtained at the top of the third distillation column by using a vapour bleed from the refrigerant fluid accumulator, this bleed being condensed and subcooled with the stages of the same refrigeration cycle, expanded to the pressure of the low pressure stage and employed for the low temperature users.

The bottom product of the fourth distillation column can be fed to a further propane/butane and heavier hydrocarbon fractionation column.

The overhead product of the fourth distillation column when it contains essentially only ethane can be deacidified by further azeotropic distillation by feeding it to a further distillation column, to obtain the ethane-carbon dioxide azeotrope as overhead product, this being recycled to the first distillation column, and a bottom product stream containing essentially ethane.

The third distillation column can be provided with a reboiler. Before being fed to the first distillation column, the gaseous hydrocarbon mixture to be fractionated can obviously be compressed or be expanded through a valve or turboexpander to the first column operating pressure, depending on the pressure at which it reaches the plant.

The following table compares the splits obtained in the individual columns:

TABLE 1

| | Known process | | Process of present invention |
|---|---|---|---|
| 1st column | | | |
| light key component | $CO_2$ | | $CO_2$ |
| heavy key component | ethane | | propane |
| 2nd column | | | |
| light key component | methane | $CH_4$ $CO_2$ | azeotrope |
| heavy key component | $CO_2$ | | $CO_2$ |
| 3rd column | | | |
| light key component | methane | | methane |
| heavy key component | $CO_2$ | $CH_4$ $CO_2$ | azeotrope |
| 4th column | | | |
| light key component | propane | | propane or butane |
| heavy key component | butane | – | butane or pentane |

The invention is described hereinafter with reference to the flow diagram of the accompanying FIG. 1 which shows a preferred embodiment of the invention but is not to be considered as limitative thereof.

The gaseous hydrocarbon mixture 1 is compressed to the working pressure in one or more stages in the compressor 2, and is then cooled in the heat exchanger 3 and dehydrated in the dehydrator 4, from which water is removed at 5. The dehydrated mixture 6 is cooled in 7 and fed to the column 8, propane and higher hydrocarbons being recovered in its rectification section and a gas 9 formed from inert gases, methane, carbon dioxide, hydrogen sulphide and ethane being obtained as overhead product. To facilitate propane recovery, the rectification section is fed with an absorbent oil produced in the plant and consisting of butane and higher hydrocarbons or pentane and higher hydrocarbons 10. The stripping section is fed with a stream 11 consisting of ethane and $CO_2$ in approximately azeotropic proportion and of absorbent oil, this stream being produced in the plant. A stream 12 consisting of ethane and higher hydrocarbons plus the absorbent oil leaves the bottom of the column 8. The column 8 is provided at its top with the condenser 13, the separator 14 and the pump 15, and at it bottom with the reboiler 16.

The stream 12 is divided into two streams 17 and 18. The stream 17 is cooled at 19 (for example with air), expanded through the valve 20 and fed to the column 21, which operates as a depropanizer or debutanizer.

The stream 18 is expanded at 22 and fed hot to the column 21. The column 21 is provided with the condenser 23, the separator 24, the pump 25 and the reboiler 26. The overhead product, i.e., the stream 27, in the form of ethane or propane and lighter hydrocarbons or butanes and lighter hydrocarbons is obtained in the liquid phase. The bottom product, i.e., the stream 28 in the form of propane and heavier hydrocarbons or butane and heavier hydrocarbons, is pumped at 29 and cooled in the heat exchanger 30.

The pumped liquid is divided into three streams. The stream 10 is injected into the column 8 to absorb the propane, the stream 31 is the heavy product (butane and higher hydrocarbons or pentane and higher hydrocarbons), and the stream 32 after further cooling in the heat exchanger 33 is injected into the condenser 34 of the distillation column 35 to absorb the ethane-carbon dioxide azeotrope.

The overhead product 9 of the column 8, which is a stream essentially free of heavy hydrocarbons, is cooled in 36 and the gas separated from the liquid in 37. The gas is partially condensed in 38 and is then fed to the "deazeotroper" column 39 in which the acid gas separation takes place. The column 39 is provided with the condenser 40, the separator 41, the pump 42 and the reboiler 43. The bottom product stream 44 of this column is formed from acid gases (carbon dioxide and hydrogen sulphide) with traces of light and heavy hydrocarbons. This stream is pumped at 45 to well injection pressure, and after recovering the cold at 46 is ready at 47 for injection into the wells. The overhead product (stream 48) is formed from all the methane and nitrogen entering the plant, plus carbon dioxide and ethane in approximately azeotropic composition. The stream 48 is compressed in the compressor 49, which is driven by the expander 50 or by an electric motor or gas turbine, to the operating pressure of the "demethanizer" column 35, to which it is fed. The cold absorption of the ethane-carbon dioxide azeotrope takes place in the column 35 using a heavy hydrocarbon stream (butane and heavier hydrocarbons or pentane and heavier hydrocarbons). To prevent any possibility of carbon dioxide solidification, the operating temperature is higher than solid $CO_2$ formation temperature. This heavy hydrocarbon stream absorbs the ethane-carbon dioxide azeotrope to allow high ethane recovery together with low carbon dioxide concentration in the processed gas.

After cooling at 33, the heavy hydrocarbon stream 32 is injected by a spray nozzle into the stream 51 leaving the top of the column 35, as it enters the condenser 34. The gas on specification is separated in the separator 52, heated in 53, expanded in the turboexpander 50, heated in 54, expanded in the turboexpander 55 and finally heated in 56 before being delivered at 57. The bottom product of the demethanizer column (stream 58), composed mainly of the ethane-$CO_2$ azeotrope and absorbent oil, is expanded through the valve 59, heated in 60 and fed at 11 to the stripping section of the "decarbonater" column 8 where the ethane is recovered.

The basic scheme can be supplemented and/or modified by partially or totally employing the following modifications (shown in dotter lines). The main modifications which can be made are as follows:

The plant inlet stream can be at high pressure as at 61 (natural gas or synthesis gas). In this case it must be cooled at 62, dehydrated at 63 and turboexpanded through 64 to the working pressure before being cooled at 7 and fed to the "decarbonater" column 8. If available at ambient temperature, as at 65, and at the pressure of the column 8 it can be directly fed after dehydration in 66.

The overhead product of the "decarbonater" column (stream 9) can be fed directly (stream 67) to the "deazeotroper" column 39, or can be partially condensed in 36 and fed (stream 68) to the column 39.

The overhead product of the "deazeotroper" column 39 (stream 48) can be fed directly without compression (stream 69) to the "demethanizer" column 35.

The delivery from the compressor 49 can be cooled in the heat exchanger 70 and fed (stream 71) to an intermediate plate of the column 35.

The "demethanizer" column 35 can be provided with a reboiler 72 to reduce the methane quantity in the stream 73 (column bottom product).

The overhead product of the "demethanizer" column 35 can be fed directly to the pipeline (stream 74).

The bottom product of the "demethanizer" column 35 after expansion through the valve 59 can be fed directly to the column 8 (stream 75).

The light hydrocarbons from the column 21 can be produced in the vapour phase at 76.

The stream 12 need not be divided into the two streams 17 and 18, but merely expanded through 22 and fed hot to the column 21.

The liquefied acid gas produced by the column 39 (stream 44), if to be fed to the flare or used in its gaseous state at low pressure, can be expanded through the valve 77 to a pressure exceeding the vapour pressure corresponding to the solid formation temperature, to recover large quantities of cold in 78 (latent heat of evaporation) which can be used in the heat exchangers 3, 13, 36, 38, 40, 70, 33, 34 and 62, the heated gas being expanded to atmospheric pressure to prevent $CO_2$ solidification. (The output acid gas is the stream 79).

The reference numeral 80 indicates the pump which feeds the liquid separated in 52 to the column 35.

A refrigeration cycle is necessary to provide the cold required by the process. This can be an absorption cycle for example using ammonia, or a mechanical compression cycle for example using ammonia or propane or freon or a mixed fluid. Of these latter a mixed fluid consisting of carbon dioxide and propane is of particular interest because these substances are already contained in the crude feed.

A cycle using propane and carbon dioxide is described hereinafter. The heat exchangers 3, 13, 36, 38, 40, 70, 33, 34, 62, 23 and 7 form part of the propane/carbon dioxide refrigeration cycle. The heat exchangers 43, 46, 72, 60, 53, 54, 56 and 78 require heat at very low temperature and can therefore take heat from the refrigeration cycle or the process.

The heat exchangers 16 and 26 require heat from an external source.

The heat exchangers 3, 19 and 30 can be cooled with air or water. FIG. 2 shows the mixed propane/carbon dioxide refrigeration cycle using plate-fin heat exchangers.

The refrigerant fluid is propane with a carbon dioxide concentration of 10% but variable from 1% to 20% according to the particular case.

The compressed fluid (compressor 81) is partially condensed in 82 and fed to an accumulator 83. The uncondensed vapour 84 is enriched in carbon dioxide.

The liquid 85 is subcooled in 86, 87 and 88. After each subcooling a part is expanded in 89, 90 and 91 and utilised for the users and for subcooling the fluid. The stream 84 enriched in carbon dioxide is liquefied and subcooled in the heat exchangers 86, 87, 88 and 92, expanded to the pressure of the low pressure stage through 93 and utilised for the low-temperature users.

The users served at the various stages are:

| high pressure stage | 3, 23, 7 |
| medium pressure stage | 13, 36, 38, 70, 33, 23 |
| low pressure stage | 40, 70, 33, 34 |

The users which can be used for heat recovery at the various stages are:

| high pressure stage | 43, 46, 72, 60, 78 |
| medium pressure stage | 60, 78 |

| | |
|---|---|
| low pressure stage | 53, 54, 56, 78 |

An example is given hereinafter to better illustrate the invention, but must not be considered as limiting the invention itself.

EXAMPLE 1

Figure 1:
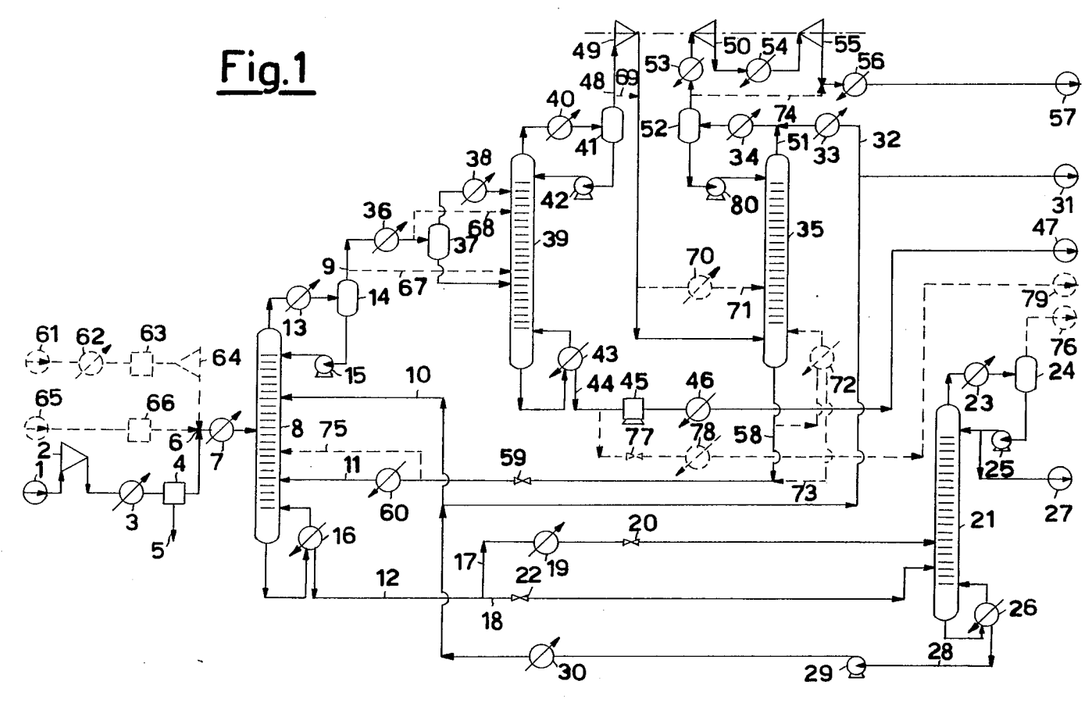
FIG. 1 shows a preferred embodiment of the invention.
Figure 2:
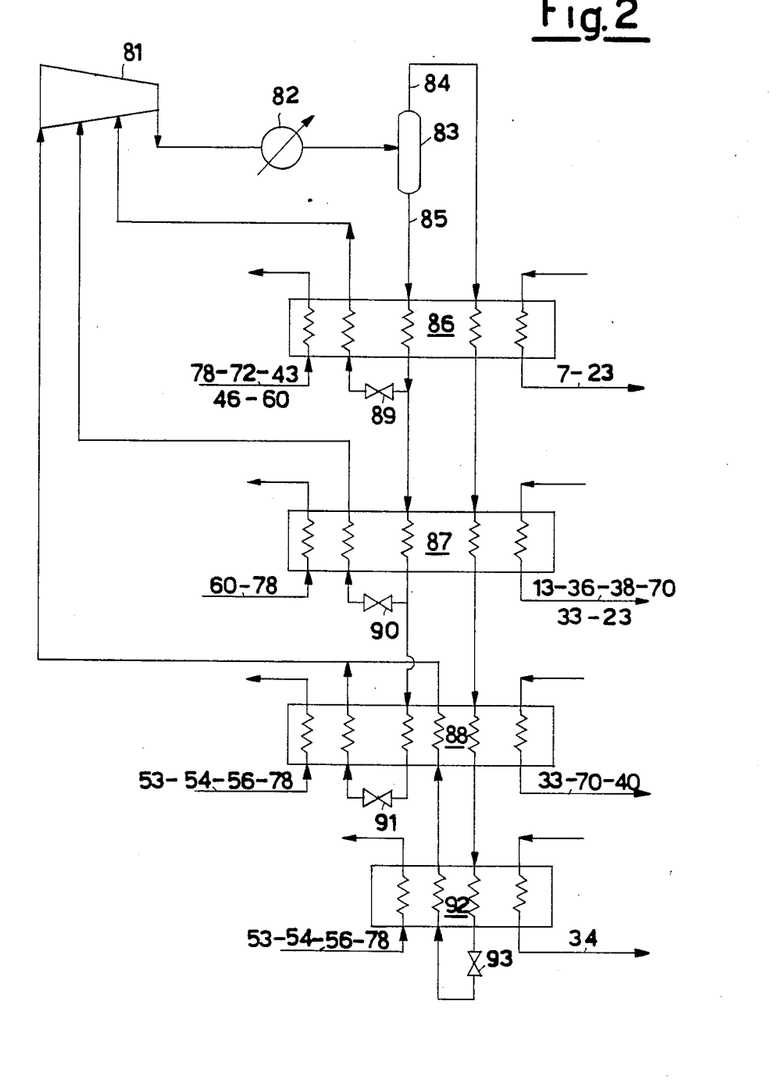
FIG. 2 shows the mixed propane/carbon dioxide refrigeration cycle using plate-fin heat exchanges.
Figure 3:
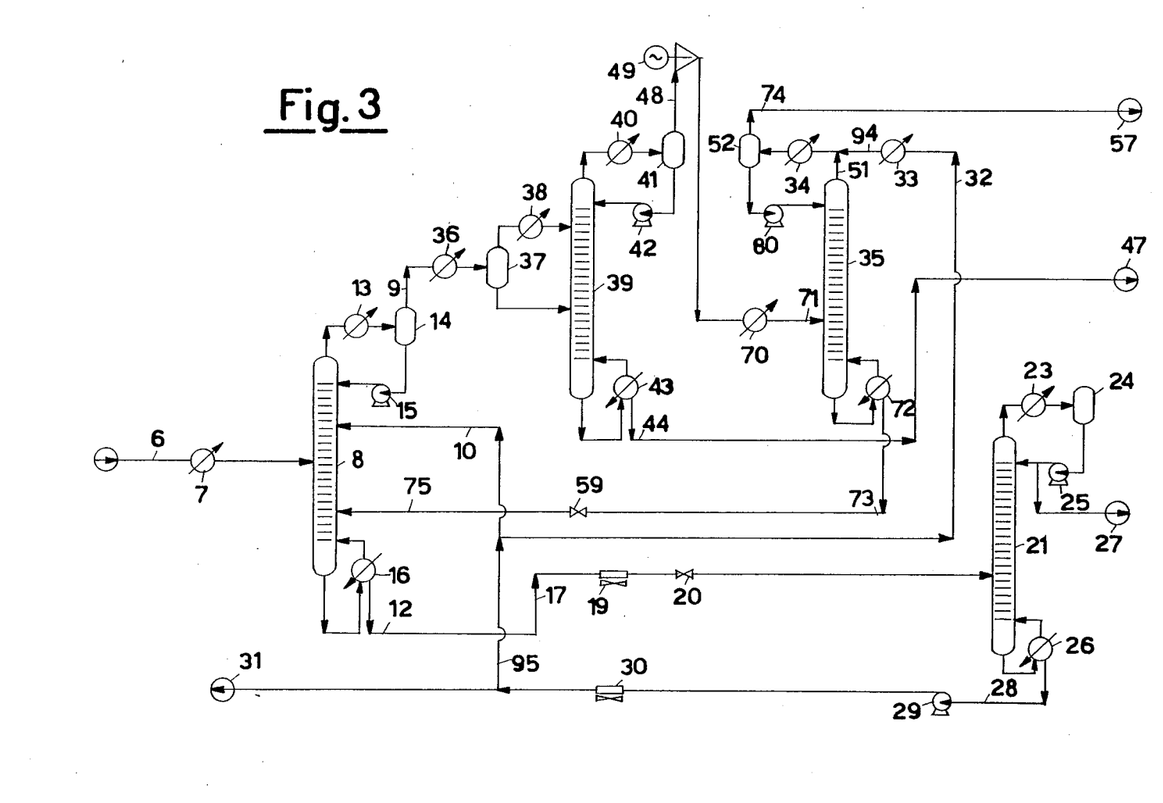
FIG. 3 is a process diagram that represents a particular case of the diagram of FIG. 1

The process diagram is shown in FIG. 3 and represents a particular case of the diagram of FIG. 1, the reference numerals having the same meaning as in FIG. 1.

An associated gas was treated from a field in which carbon dioxide gas injection was used for maximum hydrocarbon recovery. The compositions, throughputs, temperatures and pressures of the main streams are given in Table II.

The stream 94 is the stream 32 after cooling in 33. The stream 95 is part of the stream 28 (after pumping in 29 and cooling in 30). The remainder is the stream 31.

The products are as follows:
Liquid acid gases for injection into wells (stream 47)
Pipeline gas (stream 57)
Ethane, propane (stream 27)
Butane and heavier hydrocarbons (stream 31).

The acid associated gas available at 40° C. and 28.6 ata is dehydrated and further cooled in 7, and then fed to the column 8 which operates as a "decarbonater" column at a pressure of 28 ata. The column is provided with a condenser and reboiler. An absorbent oil is fed into the column rectification section and the bottom product from the demethanizer column is fed into its stripping section.

The bottom product (stream 12) of the column 8 is composed of ethane and higher hydrocarbons. This stream is cooled to a temperature of 48° C. against air and expanded to the working pressure of the "depropanizer" column 21.

The column 21 operates at a pressure of 19 ata and produces an overhead product (stream 27) consisting of ethane and liquid propane and a bottom product consisting of butane and heavier hydrocarbons (stream 28). This stream is pumped to 45 ata (pump 29), and cooled to 48° C. against air. A part of the butanes and heavier hydrocarbons (stream 31) forms the product, a further part is recycled to the decarbonater column 8 and a third part is cooled (heat exchanger 33) and injected into the condenser 34 of the demethanizer column 35.

The overhead product 9 of the decarbonater column 8, composed of methane, nitrogen, carbon dioxide, hydrogen sulphide and ethane, is partially condensed (heat exchanger 36) to a temperature of −15° C. and the separated liquid is fed to the deazeotroper (column 39). The gas is further cooled to a temperature of −20° C. and fed to the deazeotroper column 39. This column, provided with a condenser and reboiler, separates nitrogen, methane and the ethane/$CO_2$ azeotrope mixture as overhead product (stream 48) and carbon dioxide and hydrogen sulphide as bottom product (stream 44).

The deazeotroper operates at a pressure of 25.2 ata, the overhead temperature being dictated by the quantity of ethane arriving from the decarbonater. Essentially, all the ethane is recovered overhead in azeotropic mixture with the $CO_2$ and fed to the demethanizer (column 35).

The bottom product (stream 44) is the acid gas stream, which is pumped, heated and injected into the wells for heavy hydrocarbon recovery.

The stream 48 is compressed (compressor 49) to the demethanizer operating pressure (43.5 ata) (column 35), cooled in the heat exchanger 70 and fed to the demethanizer as stream 71. The hydrocarbon stream 94 is injected into this column at the condenser inlet 34 to absorb the ethane/carbon dioxide azeotrope. The overhead product (stream 57) consists of methane, nitrogen and carbon dioxide in such a quantity as to satisfy pipeline gas specifications. The bottom product (stream 73) contains ethane and carbon dioxide in addition to the fed absorbent. This stream is expanded through the valve 59 and fed to the stripping section of the decarbonater to recover the contained ethane (stream 75). (The other reference numerals have the same meaning as in FIG. 1).

The heat recovery obtainable from the user gas (stream 57) and acid gases (stream 44) has not been considered.

The refrigeration cycle used for the plant (FIG. 2) is of the propane/carbon dioxide mixture type (3% carbon dioxide). The cycle is of three stages. The refrigerant fluid condenser is a partial condenser which condenses 97.5 wt % of the fluid at 13.7 ata and 32° C.

The vapour part, enriched in carbon dioxide (13.8%) is condensed, subcooled in three stages in series and expanded to the first stage suction pressure. In this manner the required temperature can be reached for the demethanizer condenser 34.

The heat exchangers cooled by the refrigeration cycle are:

| | |
|---|---|
| high pressure stage (4.2 ata) | 23,7 |
| medium pressure stage (2.75 ata) | 3, 13, 36 |
| low pressure stage (1.45 ata) | 40, 70, 33, 34 |

The heat recoveries from the refrigeration cycle are effected in:

| | |
|---|---|
| medium pressure stage | 43, 72 |

The refrigeration cycle condenser uses water.
The heat exchangers 19 and 230 are air cooled.
The reboilers 16 and 26 use steam at 4 ata pressure.

EXAMPLE 2

(Comparative)

Figure 4:
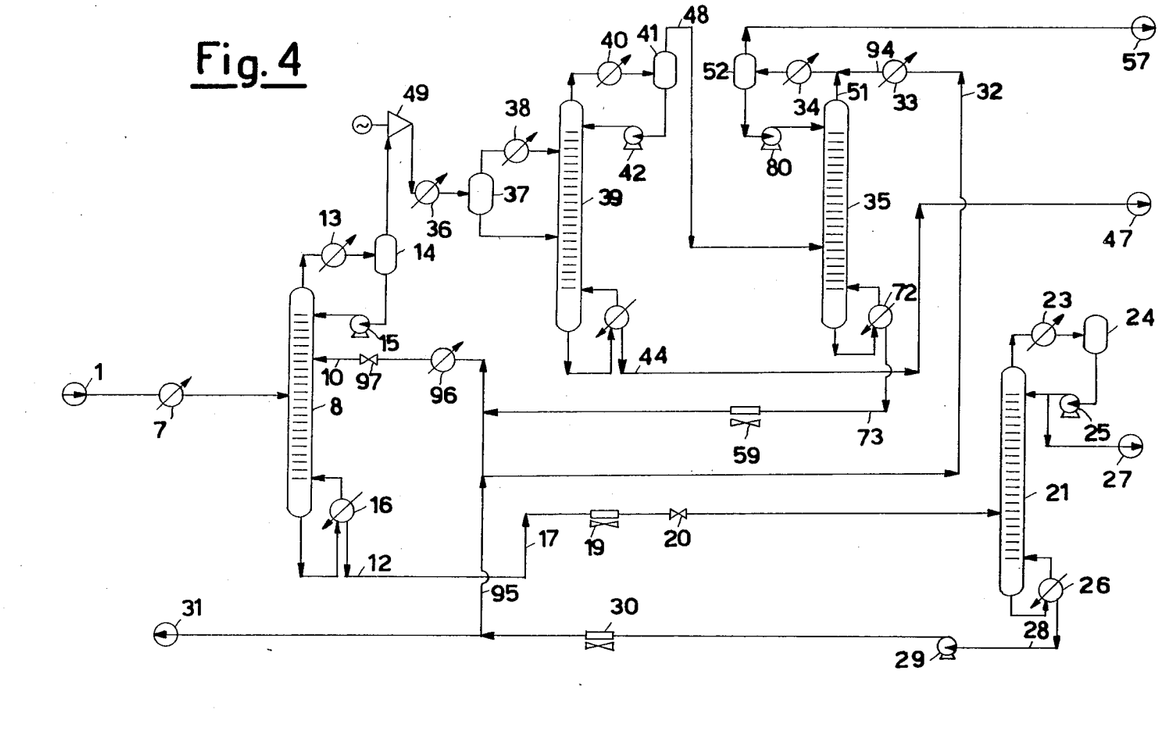
FIG. 4 is a process diagram of the known prior art.

The process flow diagram of the known art is shown in FIG. 4. The gas to be treated (stream 1) is cooled in 7 and then fed to a first column 8 with a liquid hydrocarbon stream 10, where the carbon dioxide/ethane split is done. The overhead product containing the carbon dioxide is compressed at 49 and after partial cooling is fed to a second column 39 which separates the methane (overhead product 48) from the carbon dioxide (bottom product 44). The dewpoint of the overhead product is given by a carbon dioxide content compatibile either with the temperature of the refrigeration cycle used or with the solid carbon dioxide formation temperature. This stream 48 is fed to a third column 35, also fed with a liquid hydrocarbon stream, where the final separation of methane (stream 57) from carbon dioxide (stream 73) is carried out. The bottom product 12 of the first column is fed to a fourth column 21 which separates butane (overhead product 27) from butane and heavy hydrocarbons (bottom product 28). Most of the bottom cut is recycled to the column 8 after cooling in 96 and expanding through 97, and to the column 35, the stream 31 representing the product.

The other reference numerals in the figure have the same meaning as on the preceding diagrams).

To carry out a comparison between the known art and the described process according to the invention, for the process of the known art a propane refrigeration cycle with four compression stages was used. The propane condenser uses water, the propane condensing at a pressure of 11.6 ata and a temperature of 32° C.

The heat exchangers cooled by the refrigeration cycle are:

| 1st stage (6.7 ata) | 96, 33, 7 |
| 2nd stage (3.6 ata) | 36, 33, 23 |
| 3rd stage (2 ata) | 13, 38 |
| 4th stage (1.1 ata) | 40, 34 |

The heat recoveries from the refrigeration cycle are effected in:

| 2nd stage | 43 |

The coolers 19, 30, 59 use air.

The heat exchangers 16, 72, 26 use steam at 6 ata pressure.

Table III shows the main stream compositions, throughputs, temperatures and pressures.

Table IV shows the comparison between the described process according to the invention (FIG. 3, Table II) and the known art (FIG. 4, Table III).

This comparison has been made using the same feed conditions (stream 1), product cuts (streams 57, 44, 31, 27), utilities conditions (cooling water and air) and refrigeration cycle heat recoveries.

To make the comparison more apparent the same composition has been used for the recirculating hydrocarbons (stream 32) even though in the process of the invention it is more advantageous to use a cut formed from pentanes and higher hydrocarbons.

TABLE II

| COMPONENT THROUGHPUT KMOLS/H | STREAM | | | |
|---|---|---|---|---|
| | 6 | 12 | 31 | 9 |
| NITROGEN | 16.46 | 0.00 | — | 16.46 |
| HYDROGEN SULPHIDE | 0.03 | 0.01 | — | 0.02 |
| CARBON DIOXIDE | 1167.21 | 0.50 | — | 1250.61 |
| METHANE | 57.59 | 0.00 | — | 64.60 |
| ETHANE | 41.50 | 39.02 | — | 41.37 |
| PROPANE | 31.79 | 32.17 | 0.11 | 1.81 |
| N-BUTANE | 11.57 | 210.30 | 10.19 | 0.44 |
| N-PENTANE | 3.06 | 61.59 | 2.99 | — |
| HEXANE | 0.80 | 15.50 | 0.75 | — |
| THROUGHPUT KMOLS/H | 1330.01 | 359.09 | 14.04 | 1375.32 |
| PHASE | V | L | L | V |
| TEMPERATURE °C. | 40.0 | 114.9 | 48.0 | −12.8 |
| PRESSURE ATA | 28.6 | 28.3 | 44.0 | 27.5 |

| COMPONENT THROUGHPUT KMOLS/H | STREAM | | | |
|---|---|---|---|---|
| | 48 | 44 | 71 | 73 |
| NITROGEN | 16.45 | — | 16.45 | — |
| HYDROGEN SULPHIDE | — | 0.02 | — | — |
| CARBON DIOXIDE | 84.91 | 1165.77 | 84.91 | 83.88 |
| METHANE | 64.56 | — | 64.56 | 6.99 |
| ETHANE | 39.01 | 2.34 | 39.01 | 39.01 |
| PROPANE | — | 1.81 | — | 0.59 |
| N-BUTANE | — | 0.44 | — | 54.14 |
| N-PENTANE | — | — | — | 15.95 |
| HEXANE | — | — | — | 4.00 |
| THROUGHPUT KMOLS/H | 204.93 | 1170.38 | 204.93 | 204.57 |
| PHASE | V | L | M | L |
| TEMPERATURE °C. | −37.5 | −11.6 | −53 | 21.4 |
| PRESSURE ATA | 25.0 | 25.8 | 44.0 | 43.6 |

| COMPONENT THROUGHPUT KMOLS/H | STREAM | | | |
|---|---|---|---|---|
| | 94 | 57 | 75 | 27 |
| NITROGEN | — | 16.45 | — | — |
| HYDROGEN SULPHIDE | — | — | — | 0.01 |
| CARBON DIOXIDE | — | 1.02 | 83.88 | 0.50 |
| METHANE | — | 57.55 | 6.99 | — |
| ETHANE | — | — | 39.01 | 39.03 |
| PROPANE | 0.60 | 0.02 | 0.59 | 29.86 |
| N-BUTANE | 54.41 | 0.28 | 54.14 | 0.70 |
| N-PENTANE | 15.98 | 0.02 | 15.95 | — |
| HEXANE | 4.01 | — | 4.00 | — |
| THROUGHPUT KMOLS/H | 75.00 | 75.3 | 204.57 | 70.1 |
| PHASE | L | V | M | L |
| TEMPERATURE °C. | −37.0 | −53.0 | 21.4 | 8.6 |
| PRESSURE ATA | 43.5 | 43.0 | 43.6 | 18.5 |

| COMPONENT THROUGHPUT | STREAM |
|---|---|

TABLE II-continued

| KMOLS/H | 28 | 10 | 95 |
|---|---|---|---|
| NITROGEN | — | — | — |
| HYDROGEN SULPHIDE | — | — | — |
| CARBON DIOXIDE | — | — | — |
| METHANE | — | — | — |
| ETHANE | — | — | — |
| PROPANE | 2.32 | 1.60 | 2.20 |
| N-BUTANE | 209.58 | 145.09 | 199.50 |
| N-PENTANE | 61.58 | 42.60 | 58.59 |
| HEXANE | 15.50 | 10.70 | 14.71 |
| THROUGHPUT KMOLS/H | 288.98 | 200.00 | 275.00 |
| PHASE | L | L | L |
| TEMPRERATURE °C. | 121.8 | 48.0 | 48.0 |
| PRESSURE ATA | 19.2 | 44.0 | 44.0 |

TABLE III

| COMPONENT THROUGHPUT | STREAM | | |
|---|---|---|---|
| KMOLS/H | 94 | 57 | 27 |
| NITROGEN | — | 16.44 | — |
| HYDROGEN SULPHIDE | — | — | 0.03 |
| CARBON DIOXIDE | — | 1.20 | 3.65 |
| METHANE | — | 57.46 | — |
| ETHANE | — | — | 32.57 |
| PROPANE | 1.20 | 0.03 | 30.51 |
| N-BUTANE | 108.25 | 0.65 | 0.67 |
| N-PENTANE | 32.52 | 0.05 | — |
| HEXANE | 8.03 | — | — |
| THROUGHUT KMOLS/H | 150.00 | 75.83 | 67.43 |
| PHASE | L | V | L |
| TEMPERATURE °C. | −20.0 | −35.0 | 5.5 |
| PRESSURE ATA | 41.5 | 40.5 | 18.5 |

| COMPONENT THROUGHPUT | STREAM | | |
|---|---|---|---|
| KMOLS/H | 28 | 10 | 95 |
| NITROGEN | — | — | — |
| HYDROGEN SULPHIDE | — | — | — |
| CARBON DIOXIDE | — | 46.64 | — |
| METHANE | — | 7.03 | — |
| ETHANE | — | 10.54 | — |
| PROPANE | 12.11 | 11.97 | 12.00 |
| N-BUTANE | 1092.03 | 1081.98 | 1082.60 |
| N-PENTANE | 81.06 | 80.26 | 80.25 |
| THROUGHPUT KMOLS/H | 1513.37 | 1563.53 | 1500.00 |
| PHASE | L | L | L |
| TEMPERATURE °C. | 122.0 | 16.0 | 48.0 |
| PRESSURE ATA | 19.2 | 39.6 | 44.0 |

| COMPONENT THROUGHPUT | STREAM | | | |
|---|---|---|---|---|
| KMOLS/H | 6 | 12 | 31 | 9 |
| NITROGEN | 16.46 | 0.00 | — | 16.46 |
| HYDROGEN SULPHIDE | 0.03 | 0.03 | — | 0.03 |
| CARBON DIOXIDE | 1167.21 | 3.65 | — | 1210.20 |
| METHANE | 57.59 | 0.00 | — | 64.62 |
| ETHANE | 41.50 | 32.61 | — | 19.44 |
| PROPANE | 31.79 | 42.63 | 0.10 | 1.13 |
| N-BUTANE | 11.57 | 1092.68 | 9.59 | 0.87 |
| N-PENTANE | 3.06 | 328.17 | 2.88 | — |
| HEXANE | 0.80 | 81.06 | 0.71 | — |
| THROUGHPUT KMOLS/H | 1330.01 | 1580.83 | 13.28 | 1312.75 |
| PHASE | V | L | L | V |
| TEMPERATURE °C. | 40.0 | 138.0 | 48.0 | −13.1 |
| PRESSURE ATA | 28.6 | 27.8 | 42.0 | 27.0 |

| COMPONENT THROUGHPUT | STREAM | | |
|---|---|---|---|
| KMOLS/H | 48 | 44 | 73 |
| NITROGEN | 16.45 | — | — |
| HYDROGEN SULPHIDE | — | — | — |
| CARBON DIOXIDE | 47.78 | 1162.50 | 46.61 |
| METHANE | 64.56 | — | 7.02 |
| ETHANE | 10.56 | 8.86 | 10.57 |
| PROPANE | — | 1.12 | 1.17 |
| N-BUTANE | — | 0.87 | 107.65 |
| N-PENTANE | — | — | 32.47 |
| HEXANE | — | — | 8.02 |

TABLE III-continued

| THROUGHPUT KMOLS/H | 139.35 | 1173.35 | 213.52 |
|---|---|---|---|
| PHASE | V | L | L |
| TEMPERATURE °C. | −35 | 6.7 | 64.8 |
| PRESSURE ATA | 42.0 | 42.8 | 41.1 |

TABLE IV

| | Example 2 (comparative) | Example 1 |
|---|---|---|
| Ethane recovery % | 78.5 | 94.1 |
| Propane and higher hydrocarbon recovery (Mol %) | 94.2 | 94.5 |
| Carbon dioxide recovery % | 99.6 | 99.9 |
| Recirculating hydrocarbons Ton/h (stream 32) | 93.8 | 17.2 |
| Absorbed power kW | 6150 | 5350 |
| Steam required for reboilers $10^6$ kCal/h | 18.8 | 5.3 |
| | (Psat = 6 ATA) | (Psat = 4 ATA) |

I claim:

1. A fractionation process for gaseous hydrocarbon mixtures of high acid gas content, for separating at least a fraction containing ethane, propane and heavier hydrocarbons, a fraction containing essentially acid gases and a fraction containing essentially methane and possibly inert gases, characterized by comprising the follow stages:
   (a) feeding the gaseous hydrocarbon mixture after dehydration to a first distillation column to which a heavy liquid hydrocarbon stream is fed, to obtain a gaseous overhead product stream containing methane, ethane, and acid gases and a bottom product stream containing ethane and higher hydrocarbons;
   (b) feeding the overhead product of the first distillation column to a second distillation column to obtain a gaseous overhead product stream containing methane, the ethane-carbon dioxide azeotrope and possibly light inert gases, and a bottom product stream consisting essentially of acid gases;
   (c) feeding the overhead product of the second distillation column to a third distillation column the condenser of which is injected with a liquid hydrocarbon stream, to obtain a gaseous overhead product stream consisting essentially of methane and possibly inert gases, and a bottom product stream which is recycled to the first column and contains the ethane-carbon dioxide azeotrope and the liquid hydrocarbon stream injected into the condenser;
   (d) feeding the bottom product of the first distillation column to a fourth distillation column to obtain a gaseous overhead product stream containing ethane and a bottom product stream containing higher hydrocarbons than butane.

2. A process as claimed in claim 1, wherein the overhead product of the fourth distillation column also contains propane and the bottom product also contains butane.

3. A process as claimed in claim 1, wherein the overhead product of the fourth distillation column also contains propane and butane.

4. A process as claimed in claim 1, wherein the gaseous hydrocarbon mixture to be fractionated is cooled and partially condensed before being fed to the first distillation column.

5. A process as claimed in claim 1, wherein the first distillation column operates at a pressure of between 10 and 40 ata.

6. A process as claimed in claim 1, wherein before being fed to the second distillation column, the overhead product of the first distillation column is partially condensed, the liquid obtained then being separated from the gas, which is again partially condensed, and finally the separated liquid and the partially condensed gas are fed to the second distillation column.

7. A process as claimed in claim 1, wherein the second distillation column operates at a pressure of between 10 and 50 ata.

8. A process as claimed in claim 1, wherein the overhead product of the second distillation column is compressed before being fed to the third distillation column.

9. A process as claimed in claim 8, wherein the overhead product of the second distillation column is cooled after being compressed but before being fed to the third distillation column.

10. A process as claimed in claim 9, wherein the overhead product of the second distillation column is partially condensed by the cooling, the liquid obtained then being separated from the gas, which is further condensed, the separated liquid and the partially condensed gas finally being fed to the third distillation column.

11. A process as claimed in claim 1, wherein the third distillation column operates at a temperature exceeding carbon dioxide solidification temperature.

12. A process as claimed in claim 1, wherein the liquid hydrocarbon stream injected into the condenser of the third distillation column is essentially only propane.

13. A process as claimed in claim 1, wherein the hydrocarbon stream fed to the first distillation column and/or injected into the condenser of the third distillation column is essentially only butane or only pentane or butane and higher hydrocarbons or pentane and higher hydrocarbons.

14. A process as claimed in claim 1, wherein the top of the first distillation column operates at a temperature of between −45° and +10° C.

15. A process as claimed in claim 1, wherein the top of the second distillation column operates at a temperature of between −50° and +10° C.

16. A process as claimed in claim 1, wherein the top of the third distillation column operates at a temperature of between −57° and +0° C.

17. A process as claimed in claim 1, wherein the third distillation column operates at a pressure of between 15 and 50 ata.

18. A process as claimed in claim 1, wherein the molar ratio of the hydrocarbon stream injected into the condenser of the third distillation column to the ethane-carbon dioxide azeotrope is between 0.1 and 5.

19. A process as claimed in claims 1 and 12 or 13, wherein the hydrocarbon stream injected into the condenser of the third distillation column is of different composition from the hydrocarbon stream fed to the first distillation column.

20. A process as claimed in claim 1 and 13 or 13, wherein the hydrocarbon stream injected into the condenser of the third distillation column and the hydrocarbon stream fed to the first distillation column are obtained by a fractionation run effected on the bottom product of the fourth distillation column.

21. A process as claimed in claim 1, wherein part of the bottom product of the fourth distillation column is recycled by being fed to the first distillation column and injected into the condenser of the third distillation column.

22. A process as claimed in claim 1, wherein the liquid hydrocarbon stream fed to the first distillation column is introduced into the rectification section of the column, i.e., between the feed of the gaseous hydrocarbon mixture to be fractionated and the column condenser.

23. A process as claimed in claim 1, wherein the bottom product of the third distillation column fed to the first distillation column is introduced into the first column stripping section.

24. A process as claimed in claim 1, wherein the molar ratio of the liquid hydrocarbon stream fed to the first distillation column, to the ethane in the first distillation column is between 3 and 20.

25. A process as claimed in claim 1, wherein the liquid hydrocarbon stream is fed to the first distillation column.

26. A process as claimed in claim 1, wherein the bottom product of the second distillation column is expanded and the cold produced is used to cool other process streams.

27. A process as claimed in claim 1, wherein the reboiler of the second distillation column is used to recover the cooled stream.

28. A process as claimed in claim 1, wherein the streams are cooled by using a refrigeration cycle of the mechanical compression type employing pure refrigerant fluids.

29. A process as claimed in claim 1, wherein the streams are cooled by using a refrigeration cycle of the mechanical compression type employing mixed refrigerant fluids.

30. A process as claimed in claim 29, wherein the mechanical compression refrigeration cycle uses mixed propane/carbon dioxide fluid, the required minimum temperature at the top of the third distillation column being obtained by using a vapour bleed from the refrigerant fluid accumulator, said bleed being condensed and subcooled by the stages of the refrigeration cycle itself, expanded to the pressure of the low pressure stage and used for the low temperature users.

31. A process as claimed in claim 3, wherein the bottom product of the fourth distillation column is fed to a propane/butane and heavier hydrocarbon fractionation column.

32. A process as claimed in claim 1, wherein the overhead product of the fourth distillation column is deacidified by further azeotropic distillation, by feeding it to a further distillation column to obtain as overhead product the ethane-carbon dioxide azeotrope which is recycled to the first distillation column, and as bottom product a stream containing essentially ethane.

33. A process as claimed in claim 1, wherein before feeding to the first distillation column, the gaseous hydrocarbon mixture to be fractionated is expanded through a valve or turboexpander.

34. A process as claimed in claim 1, wherein the bottom product feed is passed from the third distillation column without the aid of a reboiler.

* * * * *